US007195788B2

(12) United States Patent
Roberts

(10) Patent No.: US 7,195,788 B2
(45) Date of Patent: Mar. 27, 2007

(54) PESTICIDAL COMPOSITIONS FROM PRUNUS

(75) Inventor: Donald D. Roberts, Independence, OR (US)

(73) Assignee: Premier Botanicals, Ltd., Corvallis, OR (US)

( * ) Notice: Subject to any disclaimer, the term of this patent is extended or adjusted under 35 U.S.C. 154(b) by 303 days.

(21) Appl. No.: 10/473,548

(22) PCT Filed: Mar. 29, 2002

(86) PCT No.: PCT/US02/09677

§ 371 (c)(1),
(2), (4) Date: Sep. 29, 2003

(87) PCT Pub. No.: WO02/078451

PCT Pub. Date: Oct. 10, 2002

(65) Prior Publication Data

US 2004/0105901 A1 Jun. 3, 2004

Related U.S. Application Data

(60) Provisional application No. 60/280,606, filed on Mar. 30, 2001.

(51) Int. Cl.
*A61K 36/736* (2006.01)
(52) U.S. Cl. ...................... 424/735; 424/405
(58) Field of Classification Search ............ None
See application file for complete search history.

(56) References Cited

U.S. PATENT DOCUMENTS

| | | | |
|---|---|---|---|
| 3,624,211 A * | 11/1971 | Meiffren | 424/765 |
| 3,932,628 A * | 1/1976 | Hudson | 424/735 |
| 4,416,682 A | 11/1983 | Worthington | |
| 4,983,636 A | 1/1991 | Takeuchi et al. | |
| 5,839,224 A | 11/1998 | Emerson et al. | |
| 5,958,490 A | 9/1999 | Solar et al. | |
| 6,051,233 A | 4/2000 | Champon | |
| 6,051,612 A | 4/2000 | Borden et al. | |

FOREIGN PATENT DOCUMENTS

| JP | 60184024 | 9/1985 |
|---|---|---|
| JP | 11180879 | 7/1999 |

OTHER PUBLICATIONS

Swain et al. (Plant Physiol. (1994), vol. 106, pp. 1285-1291).*

Wilson et al., "Rapid Evaluation of Plant Extracts and Essential Oils for Antifungal Activity Against *Botrytis cinerea*," *Plant Disease*, vol. 81, No. 2, pp. 204-210 (Feb. 1997).
"Soil Amendments for Suppression of Plant Parasitic Nematodes," downloaded from http://cristel.nal.usda.gov:8080/cgi-bin/starfinder/12318/cris.txt on Jul. 23, 1999.
Soler-Serratosa et al., "Allelochemicals for Control of Plant-Parasitic Nematodes. 1. *In Vivo* Nematicidal Efficacy of Thymol and Thymol/Benzaldehyde Combinations,"*Nematropica*, vol. 26, No. 1, pp. 57-71 (1996).
Spotts et al., "Incidence and Control of Cytospora Canker and Bacterial Canker in a Young Sweet Cherry Orchard in Oregon," *Plant Disease*, pp. 577-580 (Aug. 1990).
Wilson et al., "Benzaldehyde as a Soil Fumigant, and an Apparatus for Rapid Fumigant Evaluation," *HortSciencĕ*, vol. 34, No. 4, pp. 681-685 (1999).
Hammond et al., "Volatile Aldehydes Are Promising Broad-Spectrum Postharvest Insecticides," *J. Agric. Food Chem.*, vol. 48, pp. 4410-4417 (2000).
Wilson et al., "Fruit Volatiles Inhibitory to *Monilinia fructicola* and *Botrytis cinerea*," *Plant Disease*, vol. 71, No. 4, pp. 316-319 (1987).
"Naturally Occurring Insect Control Agents and Rational Approach for Their Efficient Use," Downloaded from http://cristel.nal.usda.gov:8080/cgi-bin/starfinder/12318/cris.txt on Jul. 23, 1999.
Lowe, "Natural Plant Extracts Could Be Methyl Bromide Substitute," downloaded from http://www.ars.usda.gov/is/pr/1999/990303.htm on Mar. 17, 2000.

* cited by examiner

*Primary Examiner*—Susan Coe Hoffman
(74) *Attorney, Agent, or Firm*—Klarquist Sparkman, LLP

(57) ABSTRACT

The foliage and stems of plant species from the family Rosaceae, genus *Prunus,* yield natural pesticides when macerated. Hydrodistillation of macerated plant biomass yields a concentrated solution of organic volatile compounds that act synergistically as a natural pesticide. Volatile compounds liberated from *Prunus* biomass include 2-propanol, hexanal, trans-2-hexenal, 1-hexanol, cis-3-hexenol, mandelonitrile, benzoic acid, benzaldehyde, benzyl alcohol, hydrocyanic acid and others. These compounds may be removed from the distillate and reformulated to form a standard concentrated solution, with benzaldehyde, mandelonitrile and hydrogen cyanide being the major components. The extracts may be used as a soil treatment or soil fumigant for soil-borne pests. They also may be formulated for application as solutions with or without a surfactant or formulated as powders for foliar treatment. In a particular application, such extracts may be applied to postharvest commodities such as fruits, vegetables, roots, grains and nuts to protect against certain fungi and insects.

8 Claims, 3 Drawing Sheets

US 7,195,788 B2

PESTICIDAL COMPOSITIONS FROM PRUNUS

This is the National Stage of International Application No. PCT/US02/09677, filed Mar. 29, 2002, and claims the benefit of U.S. Provisional Patent Application No. 60/280,606, filed Mar. 30, 2001, which is incorporated herein by reference.

FIELD

The invention relates to a natural pesticide produced from the biomass of plants. The invention also relates to methods for managing and processing biomass to produce extracts that exhibit insecticidal, fungicidal, bactericidal and/or nematocidal properties.

BACKGROUND AND SUMMARY

Insects and diseases constantly threaten reduction of the value of ornamental plants and cause crop losses. Unabated, insects and diseases may significantly reduce plant survival, vigor, and yield. Synthetic chemicals are typically used to control such pests around homes, and in the agricultural and horticultural industries. However, as the general population and regulatory authorities become more sensitive to the health hazards of synthetic pesticides, more interest and effort in finding safe substitute pesticides are evident.

Replacement of synthetic pesticides with naturally occurring plant pesticide compounds may be realized in at least two ways. One way is identification of pesticidal plant compounds that can be produced synthetically in large quantities. Another is identification of potent plant extracts that may be produced from renewable sources and in sufficient quantities. The latter approach is desirable for many reasons.

Pesticidal compositions are obtained from plants in the family Rosaceae, genus *Prunus*. And methods for managing biomass for commercial scale production of pesticidal plant compositions from vegetative growth are provided. Methods for processing biomass to obtain pesticidal plant compositions and to provide an easily processed residue are also disclosed. Furthermore, methods for controlling, preventing, or curing plant diseases and infestations using plant extracts are disclosed.

DETAILED DESCRIPTION OF DISCLOSED EMBODIMENTS

Figure 1:
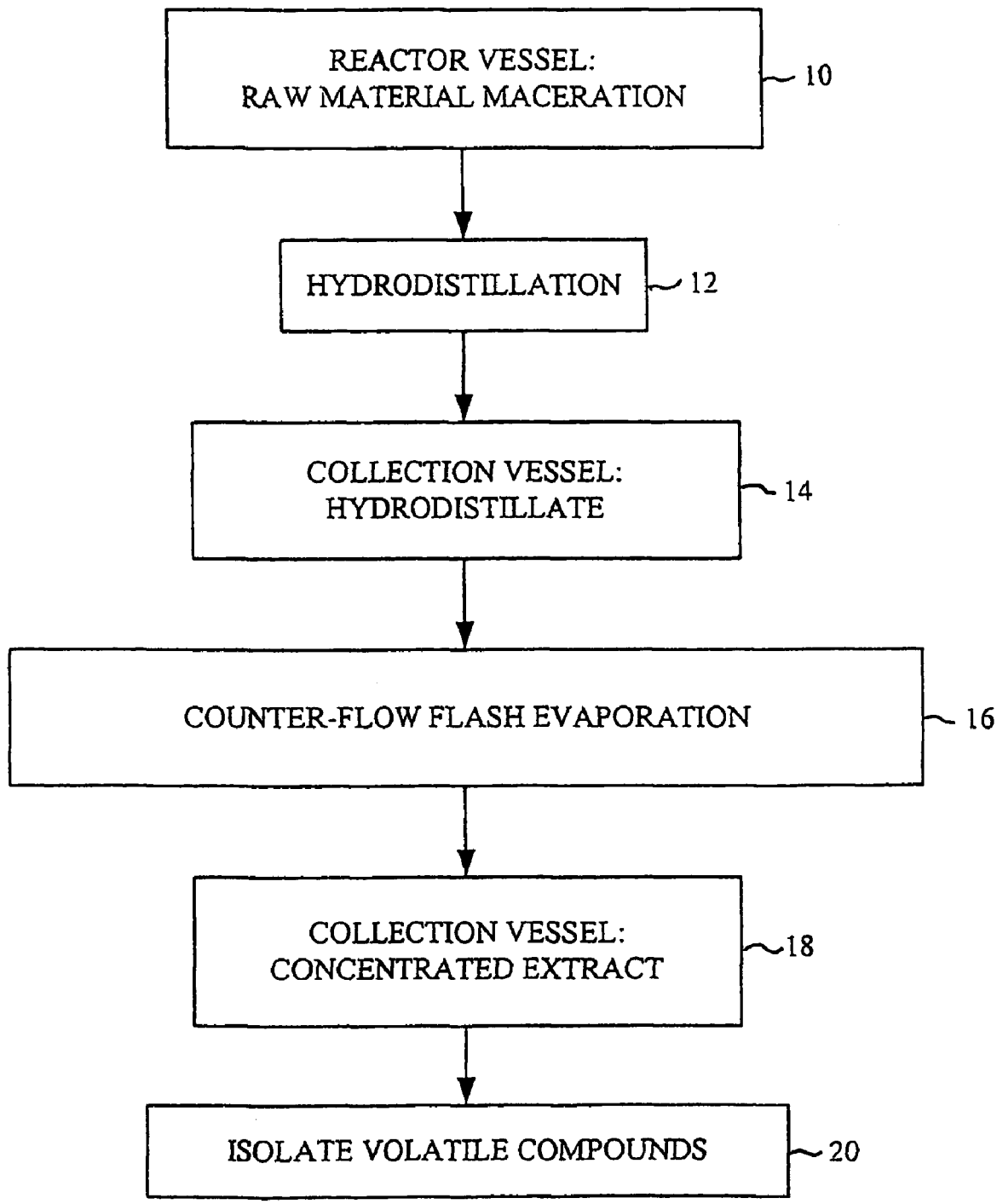
FIG. 1 is a flow diagram of a particular method of obtaining pesticidal compositions from *Prunus* biomass.

Compositions obtained from plants in the family Rosaceae, genus *Prunus*, are disclosed. In some embodiments, these compositions are mixtures of compounds extracted from *Prunus* biomass that show synergistic pesticidal activity. In particular embodiments, these compositions comprise compounds selected from the group consisting of 2-propanol, hexanal, trans-2-hexenal, 1-hexanol, cis-3-hexenol, trans-2-hexenol, mandelonitrile, benzoic acid, benzaldehyde, benzyl alcohol, and hydrocyanic acid, and mixtures thereof.

The compositions may be obtained from the reproductive and/or vegetative biomass of *Prunus* species. Representative compositions are extracted from the vegetative biomass of plants of the genus *Prunus*. In a particular embodiment, the vegetative biomass comprises *Prunus* stems and leaves. Biomass may be obtained from most *Prunus* species, including *P. serotina, P. virginiana, P. emarginata, P. dulcis*, and *P. persica*, cultivars and varieties thereof, and combinations thereof.

Methods for managing biomass for commercial scale production of pesticidal plant compositions from vegetative *Prunus* growth also are provided. In one embodiment, plants of the genus *Prunus* are planted as a row crop to facilitate harvest and maximize the biomass output of each planted acre. For example, plants may be spaced at a distance from each other that approximately accommodates growth over a certain time period such as during a spring-through-fall growing season.

Also, methods are provided for processing biomass to provide pesticidal plant compositions. In one embodiment, *Prunus* biomass is macerated to increase the concentration of desirable composition constituents, including 2-propanol, hexanal, trans-2-hexenal, 1-hexanol, trans-2-hexenol, cis-3-hexenol, mandelonitrile, benzoic acid, benzaldehyde, benzyl alcohol, and hydrocyanic acid. In other embodiments, a *Prunus* biomass macerate is hydrodistilled to provide an extract (hydrodistillate) of volatile compounds. In yet other embodiments, the volatile compounds in the hydrodistillate are further concentrated by counter-flow flash evaporation from a heated packed column to provide a concentrated extract. The solid residue remaining after maceration and/or distillation is disclosed as an easily processed substrate for production of paper and/or production of methanol.

Also described are methods for controlling, preventing, or curing diseases and insect infestations affecting plants. In one embodiment, plants are exposed to *Prunus* extracts (e.g. by contact) to control plant pests and pathogens. In a particular embodiment, a method for controlling growth of a pathogenic organism is provided wherein the pathogenic organism is exposed to a pesticidal composition obtained from *Prunus* biomass. Exposure of the pathogenic microorganism to at least a component of the composition is maintained for a time sufficient to control the growth of the pathogenic microorganism. In other particular embodiments, *Prunus* extracts are applied foliarly or directly to soil to control a disease or infestation. Extracts may also be applied to soil as fumigants or as a drench, and to foliage as a spray, mist, or drench. *Prunus* extracts may be applied to control fungal and bacterial diseases and nematode, insect and arachnid infestations.

Stored commodities such as fruit, vegetables, roots, grains and nuts may be treated with *Prunus* extracts as a in a spray, drench or fumigant to protect them from fungal infections and insect infestations to control post-harvest losses. *Prunus* extracts may be applied as an aqueous spray or may be made into a solution with an ionic, non-ionic or cationic emulsifier, such as any surfactant having an hydrophile-lipophile balance (HLB, see, for example, W. C. Griffin, J. Soc. Cosmetic Chemicals, 1: 311, 1949) of 1–20, and then applied as a spray. *Prunus* extracts may also be spray-dried and applied as a powder, for example, by incorporating the extracts into a substrate such as maltodextrin, dextrin, or disaccharide. The extracts may also be incorporated in a coating or wax used to treat foods or post-harvest commodities. *Prunus* extracts may be used for disinfection by fumigation or drench of packaging or enclosed containers that will contain foods, such as harvest bins, storage chambers and shipping containers. Fumigation may, for example, be accomplished by spraying an aqueous solution or powder, by vaporization of extracts, or by incorporating the extracts into a time-release device such as by encapsulation in a polymer matrix, polyvinylchloride strip, or rubber pellets.

A pathogenic organism selected from the group consisting of the *Phylloxera*/fungal disease complex, *Uncinula necator*, (Powdery Mildew), *Botrytis cinerea* (Botrytis Bunch Rot), *Sphaerotheca pannosa* (Powdery Mildew), a *Cytospora* species, *Cytospora chrysosperma*, a *Penicillium* species, *Penicillium expansum*, an *Alternaria* species, *Alternaria arborescens*, and combinations thereof can be treated by exposure to or contact with a *Prunus* composition. In particularly disclosed embodiments, the *Phylloxera*-fungi complex that affects grapes is treated by application of *Prunus* extracts. Application of *Prunus* extracts is also disclosed to control *Cytospora* species responsible for cankers in various trees, infection of rose plants by the powdery mildew, *Sphaerotheca pannosa*, and infection of grapes by the powdery mildew *Uncinula necator*. Such extracts are also disclosed as a fumigant for control of *Botrytis cinerea*, *Alternaria* species and *Penicillium* species.

The *Prunus* extracts may also be used as a natural topical anti-fungal agent for treating fungal diseases affecting the skin of mammals. For example, the extracts are useful for treating fungal infections that afflict human feet, such as athlete's foot, and for treating mammals afflicted with tinea.

Biomass Management

In order to provide sufficient biomass to mass-produce natural pesticidal compositions, it is desirable to grow plants in ways that maximize the amount of vegetative biomass per acre. For fruit trees, obtaining maximum vegetative biomass per acre involves planting practices that are different from those used to maximize fruit production.

Plants of the family *Rosaceae*, genus *Prunus*, can be established in a field planting such that the plants are closer to each other than the typical orchard separation of about 20 ft between individual plants. For example, from 1 foot to 10 feet between individual plants is desirable depending upon vegetative growth rate and the growth period. The spacing between plants desirably accommodates the normal growth that occurs during a particular growing period. The growing period may be a period of time from a week to a year, for example from 1 month to 8 months, such as between 2 months and 6 months. The spacing between plants also desirably accommodates mechanical harvest. For example, the plants may be planted in rows to facilitate passage of mechanized farm equipment. Plants may be cut near ground level, and the vegetative re-growth that develops from the crowns of the cut plants provides a renewable source of *Prunus* biomass. The growth that occurs during each growing period may be removed and processed to obtain pesticidal compositions.

Processing of Biomass

Plant biomass that has been chopped to increase surface area during the extraction process is mixed with water for maceration (for example, biomass that has been chopped or cut into pieces of an inch or smaller, such as $1/100$, $1/50$, $1/25$, $1/10$, $1/5$, $1/3$, or $1/2$ of an inch). Typically, just enough water is added to cover the chopped biomass. Less water will result in some of the biomass remaining unmacerated, and greater amounts of water will reduce the concentration of desirable components, thereby increasing the cost and effort needed to obtain more concentrated pesticidal compositions.

Fermentation and other natural enzymatic reactions work during maceration to break down the biomass. These reactions may be stimulated and accelerated by heating the mixture to a temperature between 25° C. and 70° C., for example, between 30° C. and 50° C. Maceration may be performed for a period of between 30 minutes and 30 hours, but may continue until particular enzymatic reactions are substantially complete. Generally, maceration at 30° C. to 50° C. for 1 hour to 18 hours, for example, for 6 hours, provides complete maceration of *Prunus* biomass.

Reactions occurring during maceration of *Prunus* biomass convert mandelonitrile glucoside to mandelonitrile. Mandelonitrile is further converted to benzaldehyde and hydrocyanic acid. Hexanal, trans-2-hexenal, 1-hexanol, trans-2-hexenol, and cis-3-hexenol are the products of the oxidative degradation of the cell-wall lipids. Benzyl alcohol is produced from benzaldehyde by alcohol dehydrogenase. It is possible to add additional enzymes to speed particular reactions and to increase or decrease the concentrations of certain components. For example, addition of alcohol dehydrogenase will decrease the concentration of benzaldehyde while increasing the concentration of benzyl alcohol hexanol and trans-2-hexenol.

The reactions that occur during maceration may be monitored to determine a time period for maceration at a particular temperature that produces a desired concentration of one or more compounds of interest. In one embodiment, the production of hydrocyanic acid is monitored to determine the maceration time. A sample of the macerate is treated with base to convert hydrocyanic acid to cyanide ions. The cyanide concentration is then determined by Liebig titration with a solution of silver ions (see, for example, Fischer and Peters, *Quantitative Chemical Analysis*, $3^{rd}$ ed., W. B. Sanders and Co., 1968, pp. 408–414). When the cyanide concentration is observed to remain substantially constant between successive samplings (e.g., every hour to several hours), the maceration step may be discontinued.

In another embodiment the hydrocyanic acid concentration during maceration is monitored using an electrode selective for a cyanide ion (VWR Scientific, West Chester, Pa.; MDA Scientific, Inc., Lincolnshire, Ill.). The concentrations of hydrocyanic acid and volatile organic compounds produced during maceration may also be monitored by gas chromatography as described in Example 1.

Following maceration, the aqueous phase contains both volatile and nonvolatile compounds extracted from the biomass. The water slurry produced by maceration of biomass (the macerate slurry) may be used, directly or diluted, as a pesticidal composition. Alternatively, the macerate slurry may be filtered to provide a filtrate (macerate solution) that may be used, directly or diluted, as a pesticidal composition and a residue of insoluble biomass. In other embodiments, the macerate solution or slurry is further processed to provide concentrated extracts of volatile components. The residue of insoluble biomass remaining after maceration is a purified composition comprising lignin and cellulose that may, for example, be easily processed into methanol or pulp for paper as a feedstock for pulping and fractionation process such as Kraft pulping, sulfite pulping or the Stake II process (see, for example, "Handbook for Pulp and Paper Technologists," G. A. Smoke, Joint Textbook Committee of the Paper Industry, $7^{th}$. Ed., 1989).

FIG. 1 presents an illustrative scheme for further processing of biomass to yield more concentrated pesticidal compositions. Maceration 10, as described above, may be followed by hydrodistillation (steam distillation) 12 of a macerate slurry or solution to provide a hydrodistillate 14. The hydrodistillate 14 is enriched in volatile compounds relative to the macerate slurry or solution. The hydrodistillate 14 may be used directly as a pesticidal composition, diluted to provide a pesticidal composition, or processed by a liquid-liquid separation method such as counter-flow flash evaporation 16 to provide a concentrated extract 18. The concentrated extract 18 may be used directly as a pesticidal composition, diluted to provide a pesticidal composition, or further enriched in volatile compounds by repeated counter-flow flash evaporation steps. In an alternative embodiment, a macerate solution is subjected to counter-flow flash evaporation 16 alone, without prior hydrodistillation 12, to concentrate volatile compounds in the *Prunus* macerate. It is also possible to purify individual compounds present in the macerate slurry or solution, the hydrodistillate, and the concentrated extract by other techniques such as distillation, column chromatography, and liquid-liquid extraction to provide compounds and mixture of compounds that exhibit pesticidal properties.

Figure 2:
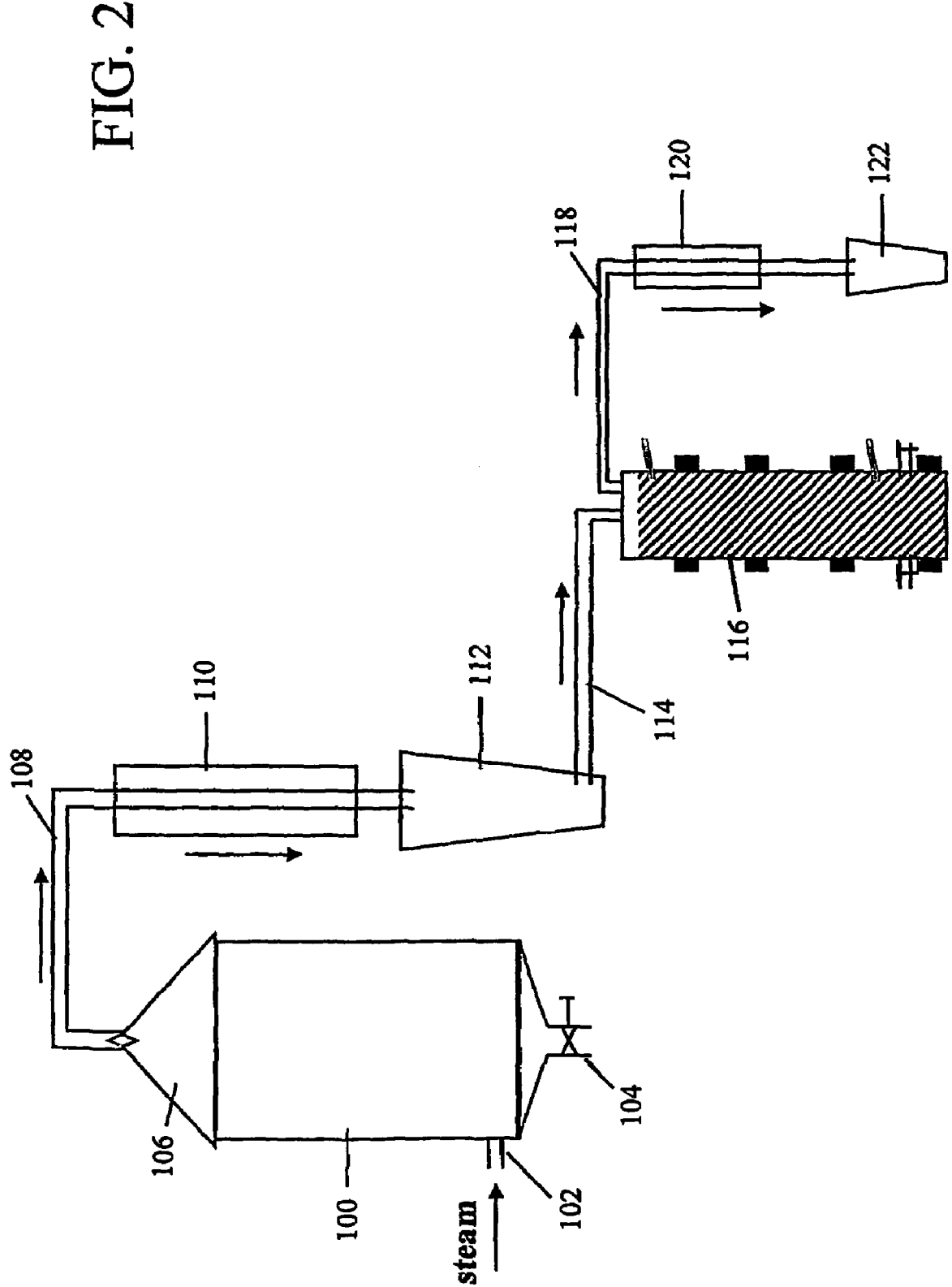
FIG. 2 is a schematic drawing showing an apparatus suitable for producing pesticidal compositions from *Prunus* biomass.

A schematic diagram of an apparatus suitable for performing the steps described above is shown in FIG. 2. With reference to FIG. 2, chopped biomass may be introduced with water into tank 100 and allowed to macerate. Alternatively, biomass may be macerated in another container to produce a macerate slurry or solution that is introduced to tank 100. Tank 100 includes a conduit 102 for introducing a supply of steam to the tank 100. Tank 100 may also include a drain 104 for removing material from the tank following hydrodistillation. Tank 100 further includes a cover 106 connected to a conduit 108. The cover 106 and conduct 108 together serve to deliver steam and volatile compounds from tank 100 to a condenser 110. Hydrodistillate, forming in condenser 110, may be collected in a collection vessel 112. Hydrodistillate collected in collection vessel 112 may be used as a pesticidal composition or routed through a conduit 114 to a counter-flow flash evaporator 116. Liquid from collection vessel 112 is introduced into the top of counter-flow-flash evaporator 116 in which the liquid is vaporized in a heated bed of column-packing material. Volatile components are entrained in an inert gas stream flowing from the bottom of the counter-flow flash evaporator 116 and that carries the components through a conduit 118 to a condenser 120. The volatile compounds are condensed (liquified) in condenser 120 and collected in a collection vessel 122 as a concentrated extract. If desired, the concentrated extract may be returned to the counter-flow flash evaporator 116 to provide an even more concentrated extract. Additional concentration steps in the counter-flow flash evaporator 116 may be performed to provide even more concentrated extracts.

Figure 3:
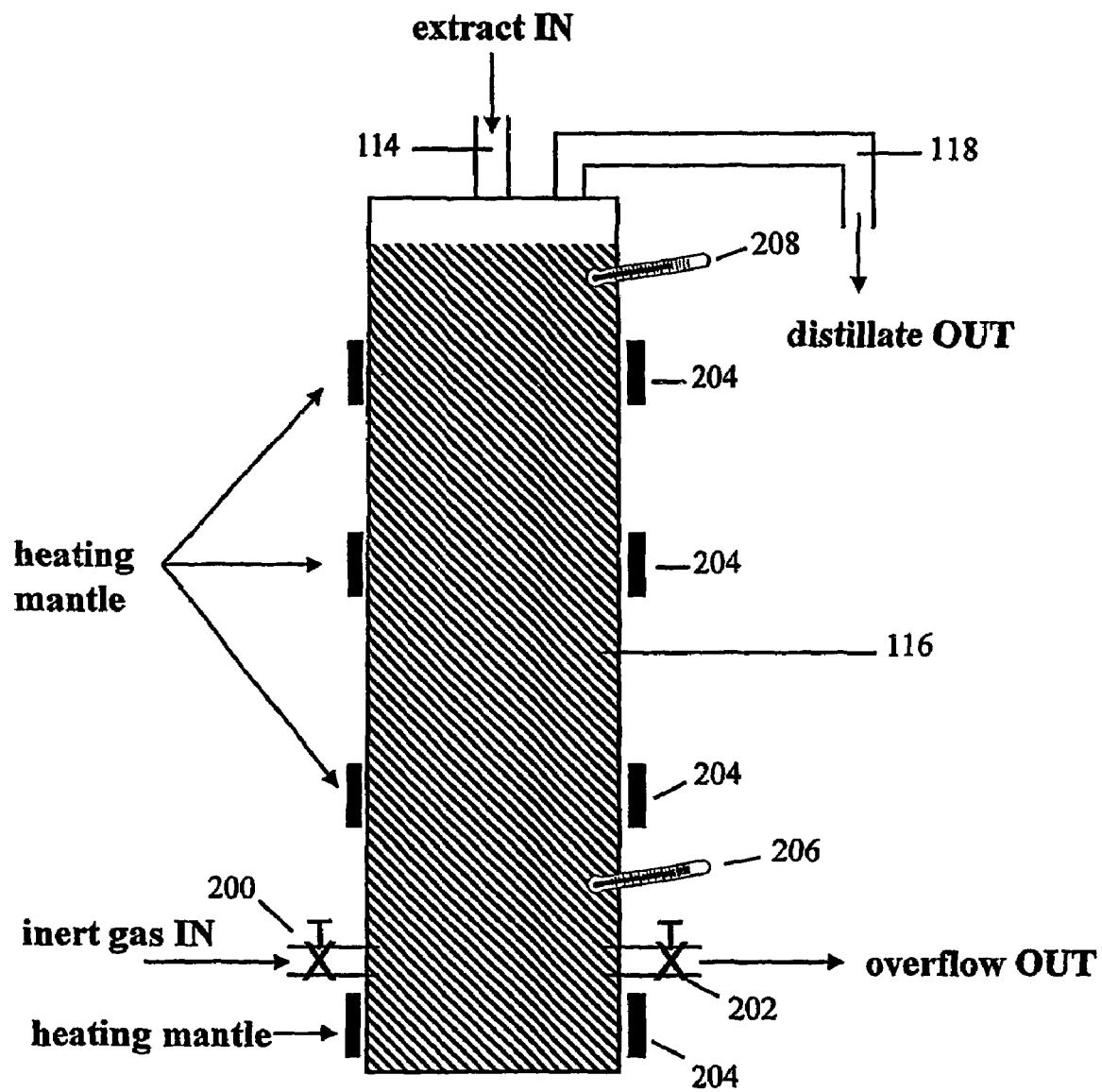
FIG. 3 is a schematic drawing of a counter-flow flash evaporation apparatus for concentrating volatile components of *Prunus* biomass.

The counter-flow flash evaporator of FIG. 2 is shown in greater detail in FIG. 3. Counter-flow flash evaporator 116 is connected to at least four conduits for facilitating fluid flow to and from the evaporator. Conduit 114 serves as an input for an aqueous composition, for example, a hydrodistillate. Conduit 118 conducts volatile compounds from the top of counter-flow flash evaporator 116. Conduit 200 provides a supply of inert gas, for example nitrogen or argon, to the base of the counter-flow flash evaporator 116. Introduction of the inert gas at the bottom of the counter-flow flash evaporator 116 sweeps volatile compounds toward the top of the evaporator 116 and into the conduit 118. A Conduit 202 is provided to drain water and nonvolatile compounds as they collect in the bottom of the counter-flow flash evaporator 116. The counter-flow flash evaporator 116 is heated by one or more heating elements 204 to establish a temperature gradient in which the temperature decreases from the location of the lower thermometer 206 to the location of the upper thermometer 208.

Pesticidal compositions comprising *Prunus* macerate slurries, macerate solutions, hydrodistillates, and concentrated extracts may be formulated with various adjuvants to aid in their stability and effectiveness as pesticides. Adjuvants include emulsifiers, surfactants (including non-ionic surfactants, cationic surfactants and anionic surfactants), stickers, stabilizers, penetrants, extenders, and corrosion inhibitors. For example, concentrated extracts may be made more water-soluble by adding of emulsifiers such as polysorbate 80. Emulsifiers include polyethyleneoxide derivatives (e.g., Tween® 20 series). Soil treatments comprising *Prunus* compositions may benefit from formulation with a soil surfactant, such as ammonium laureth sulfate, sodium laureth sulfate, nonyl phenol ethoxylate, or combination thereof. When *Prunus* compositions are applied foliarly it may be desirable to add non-ionic surfactants, such as octylphenol compounds or ethylated seed oils plus emulsifiers, to enhance spreading of the compositions on surfaces. Extenders, such as blends of organic silicone and seed oils, may be desirable to reduce volatilization of composition constituents. Likewise, addition of penetrants, such as ethoxylated and linear alcohols combined with silicone or organic silicone and esterified seed oils, desirably assist movement of the compositions into the pores of the target plant tissue.

The foregoing and additional aspects of the compositions and methods of the present inventions are further illustrated by the following Examples. The Examples are provided to assist understanding of these aspects and are not meant to limit the scope of the inventions.

EXAMPLE 1

Analysis of *Prunus* Compositions

Samples of *Prunus* biomass were macerated, either filtered or hydrodistilled, and analyzed by gas chromatography (GC). Sample analysis was performed using an HP5890 Series II (Agilent Technologies, Palo Alto, Calif.) gas chromatograph equipped with a flame ionization detector (FID). Solid-phase micro-extraction (SPME, Supelco, Bellefonte, Pa.) was used to sample the headspace over the *Prunus* compositions or was immersed in the hydrodistillate. Concentrated extracts were analyzed by direct injection into the GC. The separation of constituents was accomplished with a 30 m, 0.25 mm ID, 0.25 μm film, fused silica capillary column coated with polyethylene glycol (Supelcowax™ 10, Supelco). Splitless injection at 240° C. was used for SPME headspace analysis. Concentrated extracts (1 μL) were injected in split mode (split 100:1 at 220° C.). Oven temperature was programmed as follows: 2 min. at 40° C.; increased to 180° C. at 6° C./min; 180° C. for 8 min. The detector temperature was 250° C. and the carrier gas flow rate was 1 mL/min. Results of the GC analysis are found in Table 1.

The compounds found in the *Prunus* compositions, alone or in combination, contribute to the pesticidal properties of the extract. As Table 1 shows, the principal components are hydrocyanic acid, trans-2-hexenal, 1-hexanol, cis-3-hexenol, trans-2-hexenol, benzaldehyde, and benzyl alcohol.

The relative concentrations of these compounds (as percentages of the total volatiles) are also presented in Table 1.

TABLE 1

Chemical Composition of Biomass Extract of *Prunus* Species

| Sample** | HCN | t-2-hexenal | 1-hexenol | c-3-hexenol | t-2-hexenol | benzaldehyde | benzyl alcohol |
|---|---|---|---|---|---|---|---|
| *P. virginiana* | 0.11 | 2.68 | — | 0.12 | 0.42 | 91.23 | 0.09 |
| *P. virginiana* #2 | 0.41 | 5.16 | 0.08 | 0.08 | 0.18 | 90.22 | — |
| *P. virginiana* | 0.22 | 1.67 | — | — | 0.14 | 94.21 | 0.15 |
| *P. emarginata* | — | 3.08 | — | 0.44 | 0.55 | 92.94 | 0.46 |
| *P. emarginata* | — | 3.11 | 0.28 | .027 | 0.44 | 90.72 | 0.29 |
| *P. serotina* | 1.63 | 0.12 | — | 0.03 | 0.01 | 94.77 | 0.03 |
| *P. dulce* seedlings | 0.19 | 0.33 | 0.28 | 0.25 | 0.26 | 94.79 | 0.37 |
| *P. dulce* seedlings | 0.14 | 0.24 | — | — | — | 95.84 | 0.14 |
| *P. dulce* 14–87 selection | 0.37 | 1.36 | 0.53 | 0.52 | 0.20 | 92.72 | — |
| *P. dulce* 11–30 selection | — | 3.45 | 2.15 | 1.73 | 2.35 | 47.10 | — |

*Laboratory-distilled samples were analyzed by immersing the SPME device in 75 mL of the hydrodistillate (fiber immersed 5 min. at 25° C.). Macerated samples were analyzed by sampling headspace with SPME fiber for 1 min. at 25° C.
**Prunus virginiana* and *P. emarginata* were distilled in the pilot plant; *P. serotina* and *P. dulce* seedlings were laboratory-distilled; *P. dulce* selections were obtained by maceration followed by filtration.

EXAMPLE 2

Control of *Phylloxera* in Grapes

A grape vineyard, highly infested with *Phylloxera* and exhibiting a gradient of disease symptoms, was chosen for an evaluation of *Prunus* compositions to control damage to grapes by the soil-borne insect and its associated fungal complex. The field plot design was a complete randomized block, with three plants per treatment, four treatments per block, replicated four times. The four treatments were as follows: Treatment 1:200 mL *Prunus virginiana* hydrodistillate (collected in vessel 112 as shown in FIG. 2 and having the analysis of the first entry of Table 1), Treatment 2: 100 mL *Prunus virginiana* hydrodistillate, Treatment 3: 100 mL *Prunus virginiana* hydrodistillate plus 100 mL mint extract, Treatment 4: 100 mL water as control.

The treatments were applied by using a soil probe to open one-inch holes in the soil, 8 inches deep. Six holes were opened in a circle around each treated vine, at approximately two feet from the trunk. The treatments were applied to each hole and immediately covered with soil. The treatments were applied weekly for four weeks in May and then every two weeks during each of June, July, and August. Treatments were again applied every week for four weeks in September.

Vigor ratings were obtained prior to harvest in late September and early October. Vigor was rated on a scale of 1 to 5, with 1 representing a very weak plant and 5 representing a healthy, vigorous plant. Each plant was rated, and the respective mean vigor ratings for the three plants in each repetition are reported in Table 2. Also shown in Table 2 are the respective mean vigor ratings for all plants receiving the same treatment.

Results of the treatments indicate that application of *Prunus* compositions around the base of *Phylloxera*-infested grape plants increased vigor (Table 2). The mean vigor ratings pretreatment shows that treatment with *Prunus* extracts increased vigor in plants over control plants that only received water as a treatment. Plants receiving treatment 1 were administered twice as much *Prunus* hydrodistillate as those in treatment 2 and were slightly more vigorous on average. Plants treated with *Prunus* compositions alone (treatments 1 and 2) were more vigorous than the control plants and more vigorous than plants treated with a combination of *Prunus* composition and mint extract.

TABLE 2

Vigor of the grape variety Pinot Gris after treatment with *Prunus* Extract.

| Repetition | *Prunus* 2X | *Prunus* 1X | *Prunus* + Mint | Control |
|---|---|---|---|---|
| 1 | 3.33* | 4.00 | 1.00 | 2.00 |
| 2 | 1.50 | 1.67 | 3.67 | 1.33 |
| 3 | 3.00 | 2.00 | 3.00 | 4.17 |
| 4 | 4.67 | 4.33 | 4.00 | 4.17 |
| Mean | 3.13 | 3.00 | 2.92 | 2.92 |

*Vigor of Rating: 1 = very weak; 5 = vigorous.

At harvest, yield data were obtained by weighing the grapes from each plant. Grapes on the more stressed plants matured earlier than those on the less stressed plants. To accommodate the difference in grape maturity caused by the disease, grapes were harvested either at the end of September or approximately 2 weeks later. There was a significant difference at the $P \leq 0.05$ level between means of treatment yield and the control yield (Table 3).

TABLE 3

Fruit weight of grape variety Pinot Gris at harvest after treatment with *Prunus* Extracts.

| Repetition | *Prunus* 2X | *Prunus* 1X | *Prunus* + Mint | Control |
|---|---|---|---|---|
| 1 | 6.80 | 12.02 | 0.94 | 0.92 |
| 2 | 1.35 | 3.67 | 6.81 | 2.15 |
| 3 | 6.77 | 3.22 | 5.96 | 8.33 |
| 4 | 8.96 | 11.45 | 10.48 | 5.96 |
| Mean* | 5.97 | 7.59 | 6.05 | 4.34 |

*Mean fruit weight (lb) per plant.

EXAMPLE 3

Control of Cytospora

The air-borne fungus Cytospora sp. causes cankers on various tree crops and ornamentals (see, for example, Spotts et al., "Incidence and Control of Cytospora Canker and Bacterial Canker in a Young Sweet Cherry Orchard in Oregon," *Plant Disease*, August 1990, 577–591). *Cytospora cincta* is one of the most common canker diseases of cherry (*Prunus avium* L.). *Cytospora leucostoma* causes cankers on peach trees, and *C. chrysosperma* causes canker disease in cottonwood trees.

The effectiveness of *Prunus* compositions was compared to the effectiveness of synthetic benzaldehyde in stopping or restricting the growth of the *Cytospora* fungus on potato dextrose agar. The volatile compounds of a *Prunus virginiana* hydrodistillate were concentrated by counter-flow flash evaporation (i.e. collected from vessel 122 as shown in FIG. 2) to provide a concentrated extract that was further processed by distillation to remove hydrocyanic acid. The resulting extract was analyzed and found to contain 1.2% trans-2-hexenal, 98.5% benzaldehyde, and traces of other compounds originally in the hydrodistillate. This extract was reconstituted in distilled water to provide a solution containing approximately 10,000 ppm of *Prunus* volatiles. This stock solution was used to prepare a series of agar solutions containing between 0 and 10,000 ppm *Prunus* volatiles. The *Prunus* material was blended into the agar after autoclaving and prior to pouring the agar into Petri plates. Similarly, agar solutions containing comparable concentrations of synthetic benzaldehyde were prepared. All plates were inoculated with a 5-mm potato dextrose agar plug from a two-week-old culture of *C. chrysosperma*.

Results, presented in Table 4, show that *Prunus* volatiles, at concentrations of 1,000 ppm to 5,000 ppm in the agar growth medium, inhibit mycelia growth of *C. chrysosperma*. Both *Prunus* volatiles and synthetic benzaldehyde inhibited growth of the fungus up to and beyond 14 days at concentrations of 5,000 and 10,000 ppm, respectively. However, the *Prunus* composition inhibited the growth of the fungus more effectively than the synthetic benzaldehyde at concentrations of 500 and 1,000 ppm, indicating that the *Prunus* volatiles exhibited synergistic action relative to pure benzaldehyde.

TABLE 4

Effect of *Prunus* extract (PE) and synthetic benzaldehyde (SB) on in vitro mycelia growth of *Cytospora chrysosperma*.

| Treatment | Concentration (ppm) | Mycelial Growth (cm) Days after Treatment ||||||||
|---|---|---|---|---|---|---|---|---|---|
| | | 1 | 2 | 3 | 4 | 5 | 6 | 7 | 14 |
| SB | 0 | 0.0 | 0.8 | 2.6 | 3.5 | 4.2 | 4.1 | 4.1 | 4.1 |
| | 25 | 0.0 | 1.2 | 2.8 | 3.8 | 4.1 | 4.1 | 4.1 | 4.1 |
| | 50 | 0.0 | 1.1 | 2.6 | 3.1 | 4.0 | 4.1 | 4.1 | 4.1 |
| | 100 | 0.0 | 1.2 | 2.7 | 3.5 | 4.1 | 4.1 | 4.1 | 4.1 |
| | 500 | 0.0 | 0.9 | 2.3 | 3.1 | 4.0 | 4.0 | 4.1 | 4.1 |
| | 1,000 | 0.0 | 0.7 | 1.6 | 2.2 | 3.3 | 4.0 | 4.1 | 4.1 |
| | 5,000 | 0.0 | 0.0 | 0.0 | 0.0 | 0.0 | 0.1 | 0.3 | 0.0 |
| | 10,000 | 0.0 | 0.0 | 0.0 | 0.0 | 0.0 | 0.0 | 0.0 | 0.0 |
| PE | 0 | 0.0 | 0.8 | 2.6 | 3.5 | 4.2 | 4.1 | 4.1 | 4.0 |
| | 25 | 0.0 | 1.0 | 2.6 | 3.7 | 4.1 | 4.1 | 4.1 | 4.0 |
| | 50 | 0.0 | 1.0 | 2.6 | 3.7 | 4.0 | 4.1 | 4.1 | 4.1 |
| | 100 | 0.0 | 2.4 | 2.7 | 3.7 | 4.1 | 4.1 | 4.2 | 4.1 |
| | 500 | 0.0 | 0.8 | 1.1 | 2.9 | 4.0 | 4.1 | 4.1 | 4.1 |
| | 1,000 | 0.0 | 0.2 | 0.7 | 1.2 | 2.1 | 2.9 | 3.3 | 4.1 |
| | 5,000 | 0.0 | 0.0 | 0.0 | 0.0 | 0.0 | 0.0 | 0.0 | 0.0 |
| | 10,000 | 0.0 | 0.0 | 0.0 | 0.0 | 0.0 | 0.0 | 0.0 | 0.0 |

Each value is numerical radial growth of mycelium in centimeters and is an average of two tests, each with two replicate plates. Petri plates were 8.5 cm in diameter. SB and PE were incorporated into PDA medium after autoclaving and prior to pouring plates. 5 mm PDA plugs of 14-day-old cultures of *Cytospora chrysosperma* were centrally placed in plates and allowed to grow for 14 days at 23° C.

EXAMPLE 4

Control of Powdery Mildew in Grapes

Powdery mildew is a problem on most *Vitis vinifera* (European) varieties of grape. The casual organism is *Uncinula necator*, a fungus that overwinters as hyphae inside dormant buds or as cleistothecia on the surface of the vine. The fungus becomes active as soon as buds break in the spring, and covers the new shoots. It is important to control the fungus early to prevent serious vine damage. The fungus can attack all above-ground plant parts.

*Prunus* compositions (including crude *Prunus virginiana* hydrodistillate, collected in vessel 112 of FIG. 2, having the analysis of the first entry of Table 1) were tested on grape plants (Pinot Noir) infected with powdery mildew. The experiment was set up in a complete randomized block design with three repetition, four treatments each, with three observations per treatment. Treatments were as follows: Prunus 1: crude hydrodistillate from *Prunus* biomass, Prunus 2: benzaldehyde separated from the hydrodistillate at 1,000 ppm, SB-synthetic benzaldehyde, and control-distilled water.

Treatments were applied to infected leaves in early August and in early September. Three adjacent leaves on a vine were sprayed with each treatment and replicated on three different vines (plants). The solutions were applied with a mist sprayer until run off. The first disease reading was obtained in early September, one month after the first treatment application. The second disease reading was obtained in early October, about one month after the second treatment application.

Disease ratings were based on a scale of 1 to 5, with 1 indicating no symptoms and 5 indicating 100-percent infected. The results are summarized in Table 5, in which each datum is a mean value of the three observations for each treatment made on the two dates disease readings were obtained. The crude *Prunus* hydrodistillate (treatment Prunus 1) inhibited the growth of the fungus with only minor symptoms of rot present by the second reading. Treatments *Prunus* 2 and SB reduced the spread of the mildew fungus, but did not control it. The crude hydrodistillate composition contained all of the volatile chemicals identified above in Example 1. The increased fungicidal action of the crude hydrodistillate indicated synergistic action of the *Prunus* volatiles relative to purified or synthetic benzaldehyde.

TABLE 5

Effect of *Prunus* extracts on powdery mildew (*Uncinula necator*) development on 'Pinot Noir' grape leaves.

|  | Control | | *Prunus* 1 | | *Prunus* 2 | | SB | |
| --- | --- | --- | --- | --- | --- | --- | --- | --- |
| Repetition | 9/7 | 10/5 | 9/7 | 10/5 | 9/7 | 10/5 | 9/7 | 10/5 |
| 1 | 4 | 4 | 1 | 1 | 1 | 3 | 2 | 3 |
| 2 | 3 | 4 | 1 | 2 | 1 | 3 | 1 | 3 |
| 3 | 3 | 5 | 1 | 2 | 2 | 3 | 2 | 3 |

*Prunus* 1: crude water distillate,
*Prunus* 2: 1000 ppm *Prunus* extract,
SB: synthetic benzaldehyde at 1000 ppm.
Scale ratings: 1 = no symptoms, 5 = 100% infected.

EXAMPLE 5

Control of Powdery Mildew in Rose

Powdery mildew of Rose (Rosa sp.) is caused by a fungal pathogen (*Sphaerotheca pannosa*) that overwinters in infected buds, leaves, twigs, and branches. The disease is a problem in most growing regions on susceptible varieties. It has multiple disease cycles in a growing season and develops in moist to dry environments. Infection can cause the foliage to be stunted or even drop from the plant.

*Prunus* compositions (including crude *Prunus virginiana* hydrodistillate, collected in vessel 112 of FIG. 2, having the SPME determined composition of the first entry in Table 1) were tested on diseased plants and were evaluated as a fungicide for controlling Rose powdery mildew. The experiment was set up in a complete randomized block design with three repetitions and four treatments. Treatments were as follows: *Prunus* 1: crude hydrodistillate from *Prunus* biomass, *Prunus* 2: benzaldehyde separated from the crude hydrodistillate at 1,000 ppm, SB-synthetic benzaldehyde, and control-distilled water.

Treatments were applied to infected leaves twice (one week apart) in late July, and once in late August. All leaves were covered with mildew mycelia at the time of the first treatment. One compound leaf was treated with each treatment. Leaves from different stems were treated for each of the three repetition. The treatments were applied with a mist sprayer until run off. Disease development was rated on a scale of 1 to 5, where 1 indicated no symptoms and 5 indicated 100-percent infected. The first disease rating was obtained at the time of the late August treatment, followed by a second disease rating in early September. Treatment *Prunus* 1 (the crude hydrodistillate) was the most effective of the treatments in controlling the rose mildew fungus (Table 6). The crude distillate from the *Prunus* biomass was effective in eliminating or inhibiting the growth of the fungus on the rose leaves. The extracted benzaldehyde (treatment *Prunus*-2) and the synthetic benzaldehyde (treatment SB) were less effective in removing the fungus from the infected rose leaves. The crude hydrodistillate containing all of the volatile compounds identified in Example 1 appeared to act synergistically, relative to purified or synthetic benzaldehyde, to control the rose mildew fungus.

TABLE 6

Effect of *Prunus* extracts on powdery mildew (*Sphaerotheca pannosa*) development on rose leaves.

|  | Control | | *Prunus* 1 | | *Prunus* 2 | | SB | |
| --- | --- | --- | --- | --- | --- | --- | --- | --- |
| Repetition | 8/22 | 9/4 | 8/22 | 9/4 | 8/22 | 9/4 | 8/22 | 9/4 |
| 1 | 4 | 5 | 2 | 2 | 4 | 4 | 3 | 3 |
| 2 | 3 | 3 | 1 | 1 | 2 | 2 | 3 | 2 |
| 3 | 5 | 5 | 2 | 1 | 3 | 4 | 2 | 3 |

*Prunus* 1: crude water distillate,
Prunus 2: 1000 ppm *Prunus* extract,
SB: synthetic benzaldehyde at 1000 ppm.
Scale ratings: 1 = no symptoms, 5 = 100% infection.

EXAMPLE 6

Control of Post-Harvest Decay

Several fungal and bacterial diseases may cause post-harvest decay of fruits and vegetables. *Botrytis cinerea*, *Alternaria arborescens*, and *Penicillium expansum* are exemplary causal agents of post-harvest decay.

*Botrytis cinerea* and *Penicillium expansum* were isolated from a decaying tomato and *Alternaria arborescens* was provided by the USDA/ARS Tree Fruit Research Lab in Wenatchee (Wash.). The fungi were cultured in 9-cm diameter Petri plates on potato dextrose agar (PDA) at room temperature. Each Petri dish held 10 μL of a concentrated *Prunus* extract (*Prunus virginiana* hydrodistillate concentrated by counter-flow flash evaporation and composed primarily of 1.2% trans-2-hexenal and 98.5% benzaldehyde) absorbed into a 1-cm #3 paper filter and placed on the top of a 5×5 mm glass cylinder in the center of the Petri plate. Plates were inoculated with a fungal plug containing both spores and mycelium. Fungal growth was observed every two days after inoculation.

The *Prunus* composition showed fungicidal activity against *Botrytis cinerea*, and fungistatic activities against *Penicillium expansum* and *Alternaria arborescens* (Table 7).

TABLE 7

Effect of *Prunus* extract on inhibition of *Botrytis cinerea*, *Penicillium expansum*, and *Alternaria arborescens*. 0 = no growth; 5 = 100% plate covered.

|  | Days after inoculation | | | |
| --- | --- | --- | --- | --- |
|  | 2 | 7 | 9 | 14 |
| *Botrytis cinerea* | 0 | 0 | 0 | 0 |
| *Penicillium expansum* | 0 | 1 | 1.5 | 4 |
| *Alternaria arborescens* | 0 | 0.5 | 2.5 | 5 |
| Control* | 1 | 5 | 5 | 5 |

*Growth rate was similar for all three fungi in the control plate without *Prunus* vapor It should be recognized that the illustrated embodiments are only particular examples of the inventions and should not be taken as a limitation on the scope of the inventions. Rather, the inventions include all that comes within the scope and spirit of the following claims.

The invention claimed is:

1. A method for controlling growth of a pathogenic organism, comprising exposing the pathogenic organism to a pesticidal composition obtained from a hydrodistillate of *Prunus* biomass in an amount and for a time sufficient to control the growth of the pathogenic organism, wherein the hydrodistillate comprises at least two compounds selected from the group consisting of 2-propanol, hexanal, trans-2-hexenal, 1-hexanol, cis-3-hexenol, trans-2-hexenol, mandelonitrile, benzoic acid, benzaldehyde, benzyl alcohol, and hydrocyanic acid;

wherein the pathogenic organism is selected from the group consisting of *Phylloxera, Uncinula necator, Botrytis cinerea, Sphaerotheca pannosa,* a *Cytospora* species, *Cytospora chrysosperma,* a *Penicillium* species, *Penicillium expansum,* an *Alternaria* species, and *Alternaria arborescens;* and wherein the *Prunus* species is selected from the group consisting of *P. serotina, P. virginiana, P. emarginata, P. dulcis,* and *P. persica.*

2. The method of claim 1, wherein the *Prunus* biomass is macerated prior to hydrodistillation.

3. The method of claim 1, wherein the *Prunus* biomass is stems and leaves of plants of the *Prunus* species.

4. The method of claim 1, wherein the hydrodistillate comprises hydrocyanic acid, trans-2-hexenal, 1-hexanol, cis-3-hexenol, trans-2-hexenol, benzaldehyde, and benzyl alcohol.

5. The method of claim 1, wherein the hydrodistillate comprises trans-2-hexenal and benzaldehyde.

6. The method of claim 1, wherein the hydrodistillate consists of at least two compounds selected from the group consisting of 2-propanol, hexanal, trans-2-hexenal, 1-hexanol, cis-3-hexenol, trans-2-hexenol, mandelonitrile, benzoic acid, benzaldehyde, benzyl alcohol, and hydrocyanic acid.

7. The method of claim 1, wherein the hydrodistillate consists of hydrocyanic acid, trans-2-hexenal, 1-hexanol, cis-3-hexenol, trans-2-hexenol, benzaldehyde, and benzyl alcohol.

8. The method of claim 1, wherein the hydrodistillate consists of trans-2-hexenal and benzaldehyde.

* * * * *